US011801063B2

(12) United States Patent
Tsai et al.

(10) Patent No.: US 11,801,063 B2
(45) Date of Patent: Oct. 31, 2023

(54) FLEXIBLE GUIDE FOR APPLICATION OF BONE PLATES

(71) Applicant: Revelation Plating, LLC, Clackamas, OR (US)

(72) Inventors: Stanley Tsai, Clackamas, OR (US); Michael Bottlang, Clackamas, OR (US); Steven Madey, Clackamas, OR (US)

(73) Assignee: Revelation Plating, LLC, Clackamas, OR (US)

( * ) Notice: Subject to any disclaimer, the term of this patent is extended or adjusted under 35 U.S.C. 154(b) by 351 days.

(21) Appl. No.: 17/317,667

(22) Filed: May 11, 2021

(65) Prior Publication Data

US 2021/0259712 A1 Aug. 26, 2021

Related U.S. Application Data

(63) Continuation of application No. 16/445,024, filed on Jun. 18, 2019, now Pat. No. 11,033,284.

(60) Provisional application No. 62/686,108, filed on Jun. 18, 2018.

(51) Int. Cl.
| *A61B 17/17* | (2006.01) |
| *A61B 17/80* | (2006.01) |
| *A61B 17/68* | (2006.01) |
| *A61B 17/88* | (2006.01) |
| *A61F 2/46* | (2006.01) |

(52) U.S. Cl.
CPC ...... *A61B 17/1728* (2013.01); *A61B 17/1796* (2013.01); *A61B 17/8061* (2013.01); *A61B 17/1725* (2013.01); *A61B 17/8875* (2013.01); *A61B 2017/681* (2013.01); *A61F 2/4603* (2013.01)

(58) Field of Classification Search
CPC ............... A61B 17/1728; A61B 2017/681
See application file for complete search history.

(56) References Cited

U.S. PATENT DOCUMENTS

| 2,494,229 A * | 1/1950 | Collison | A61B 17/8635 408/72 R |
| 2005/0085818 A1* | 4/2005 | Huebner | A61B 17/1728 606/291 |
| 2007/0239158 A1* | 10/2007 | Trieu | A61B 17/7059 606/279 |
| 2011/0004254 A1* | 1/2011 | Beger | A61B 17/1728 606/289 |
| 2012/0053587 A1* | 3/2012 | Kiritsis | A61B 17/17 606/71 |
| 2013/0060288 A1 | 3/2013 | Rodgers et al. | |

(Continued)

FOREIGN PATENT DOCUMENTS

CN 201524133 7/2010

*Primary Examiner* — Christian A Sevilla

(74) *Attorney, Agent, or Firm* — Schwabe, Williamson & Wyatt, PC

(57) ABSTRACT

Embodiments herein employ a flexible orthopedic alignment guide for surgical implantation of flexible bone plates. Specifically, the alignment guide is designed to be used in conjunction with flexible bone plates whereby flexible sections of the alignment guide aid in alignment of drill bits and fasteners with the fastener holes of the bone plate. The flexible guide is designed to flex in a similar manner to the bone plate, thus maintaining positive engagement without compromising hole alignment.

7 Claims, 3 Drawing Sheets

(56) References Cited

U.S. PATENT DOCUMENTS

2016/0051297 A1\* 2/2016 Steffensmeier ...... A61B 17/808
　　　　　　　　　　　　　　　　　　　　606/86 B
2016/0089190 A1 3/2016 Taber \* cited by examiner

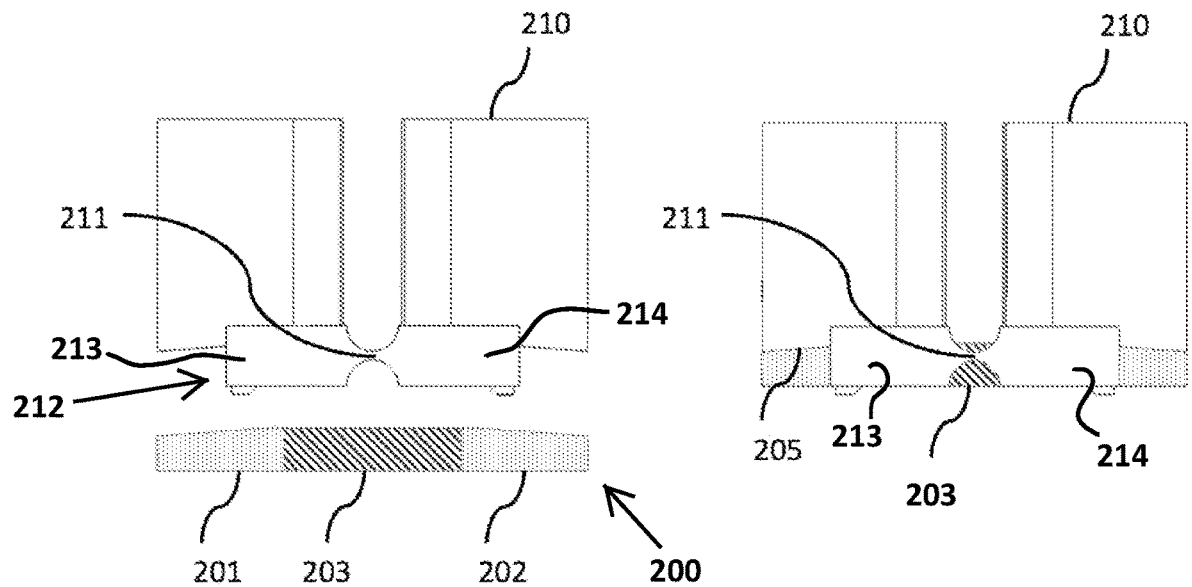
Figure 2A
Figure 2B
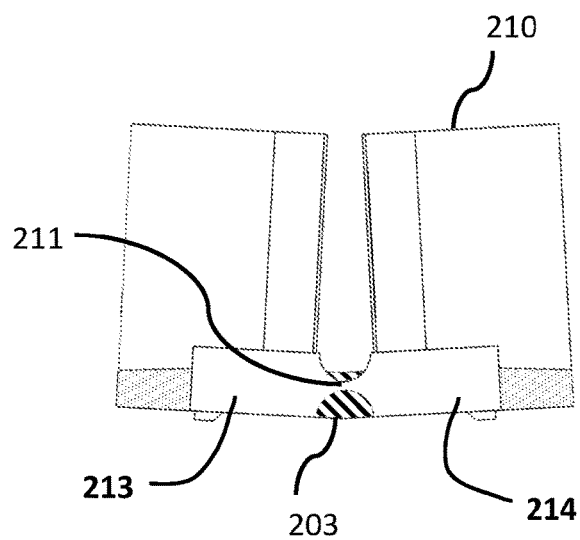
Figure 2C

FLEXIBLE GUIDE FOR APPLICATION OF BONE PLATES

CROSS-REFERENCE TO RELATED APPLICATION

The present application is a U.S. Continuation Patent Application which claims priority to U.S. patent application Ser. No. 16/445,024 filed Jun. 18, 2019 and claims the priority benefit of the earlier filing date of U.S. Provisional Application No. 62/686,108, filed Jun. 18, 2018, both of which are hereby incorporated herein by reference in their entireties.

TECHNICAL FIELD

Embodiments herein relate to a flexible guide for aligning with a flexible bone plate.

BACKGROUND

The sternum is a bony structure that connects ribs at the front of the chest wall. A sternotomy is a surgical procedure in which the sternum is cut along its longitudinal midline. A sternotomy is performed to gain access to the thoracic cavity for surgery on the heart, lungs, or other inner organs.

After a sternotomy has been performed, the divided sternum must be reconnected, or "closed", in a sufficiently stable manner to allow for bony healing of the sternotomy cut. Closure of a sternal osteotomy has traditionally been performed using stainless steel wires that are circumferentially wrapped around the sternum or through the sternum. To provide a simpler and more durable fixation, rigid metallic plates and clamps for sternal closure have been developed that attach to the front of the sternum. Clinical studies have shown that compared to traditional wire cerclage, repair of a sternal osteotomy with rigid plates provides more stable fixation and leads to better healing, whereby patients experience less pain and require less narcotic medication. In some novel sternum plate designs, the plate is engineered to be flexible at the midline to allow for contouring of the plate to the bony anatomy, reduce the stress on the screws, and improve the healing of the sternal osteotomy by allowing controlled motion between the sternum halves.

Current rigid plates may include rigid instrumentation that engages the plate to help guide the drill or screws for optimal alignment. For flexible plate designs, rigid instrumentation would inhibit the ability of the surgeon to contour the plate during surgery, and may place additional stresses on the screw-bone interface by preventing optimal seating of the plate during implantation.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIG. 2A illustrates the longitudinal end view of the alignment guide and plate prior to engagement of the alignment guide to the plate;

FIG. 2B illustrates the longitudinal end view of the alignment guide and plate after engagement of the alignment guide to the plate;

FIG. 2C illustrates the longitudinal end view of the alignment guide and plate after bending of the device.

DETAILED DESCRIPTION OF DISCLOSED EMBODIMENTS

Figure 1:
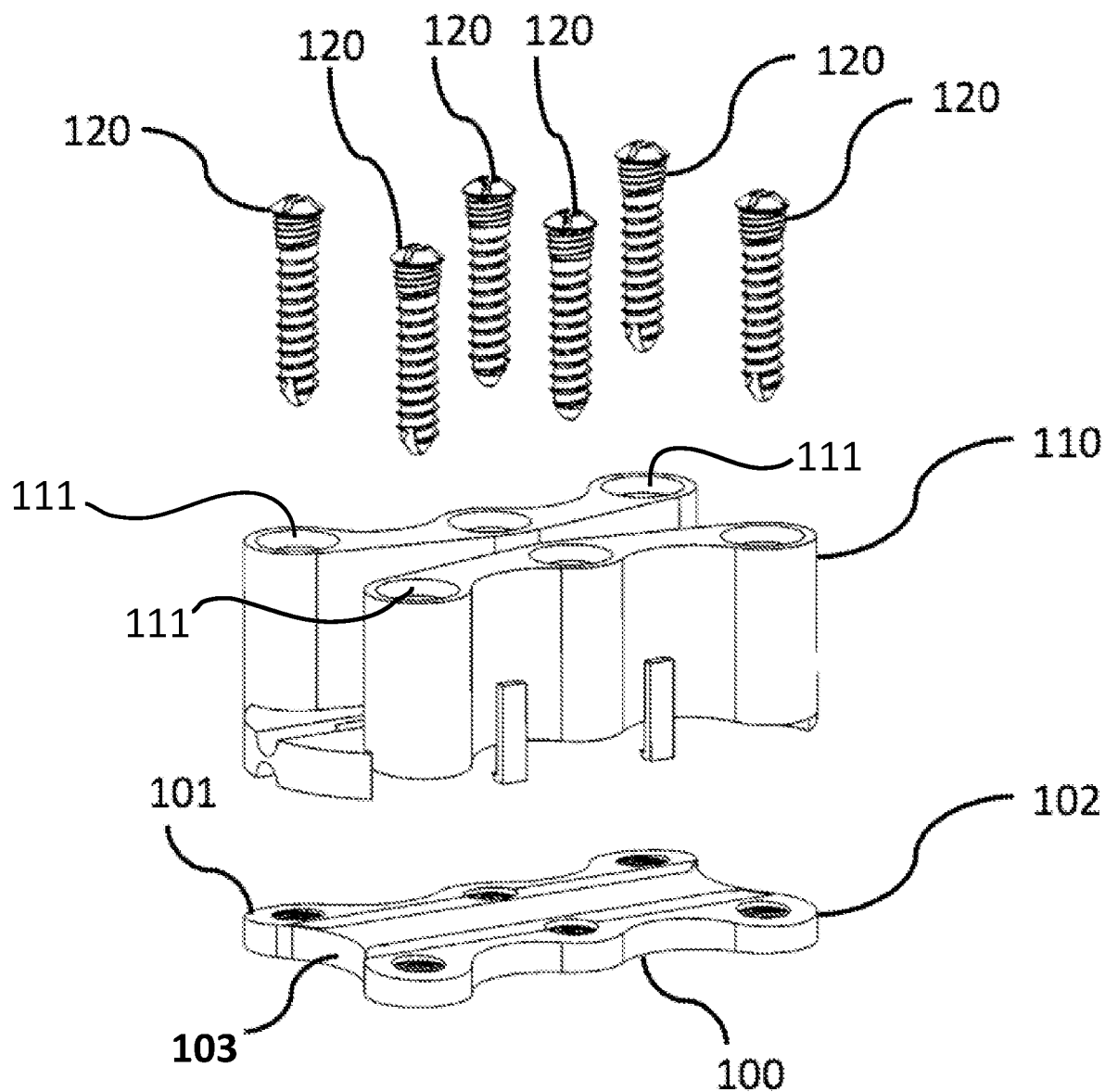
FIG. 1 illustrates an exploded view of the fasteners, alignment guide, and flexible plate.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Embodiments of the present invention address the need for flexible guiding instrumentation that allows for analogous flexion of a flexible bone plate to allow the surgeon to take advantage of the benefits of flexibility within the plate.

The guiding instrumentation may take the form of a drill guide or a screw guide, which are commonly used surgical instruments. By allowing the alignment guide to mirror the flexion of the plate, the instruments can perform their intended purpose of optimally aligning the drill bit or screw to the screw hole even when the plate is deformed from its nominal shape to conform to the bony anatomy.

Thus, embodiments provide a flexible alignment guide that engages a flexible bone plate, such as a chest wall/sternal fixation plate, and accurately aligns a drill bit or screw with the screw holes within the flexible plate even when the plate is deformed from its nominal shape.

Embodiments herein may be used with a flexible chest wall/sternal fixation plate, as well as with other bones, such as long bones.

The present disclosure describes an alignment guide that is able to engage flexible bone plates, and maintain proper alignment even when the bone plate is deformed from its nominal shape. Some novel bone plates, such as described in U.S. patent application Ser. No. 16/315,107, filed on Jan. 3, 2019, which is hereby incorporated by reference in its entirety, allow for flexibility within the plate, allowing for motion to trigger callus formation through secondary bone healing and improved conformity to the bony anatomy without necessitating plate bending instrumentation during surgery. For these designs, it is imperative that any guidance instrumentation also allow for flexibility in order to accurately align with the fastener/screw holes within the plate. If the alignment guide was rigid, it would restrict flexibility of the plate, have difficulty staying engaged on the plate, or may inaccurately target the fastening holes if the plate were deformed from its initial shape.

The use of a flexible alignment guide is counter-intuitive since bone plates are typically designed to be rigid to provide fixation of the bone fragments. The use of a flexible alignment guide would frustrate the intended purpose of such instruments, which is to provide rigid guidance of a drill, drill bit, or screw with the plate fastener hole. The use of a flexible guide with a rigid plate could lead to malalignment of the drill, drill bit, or screw. When used in combination with a flexible plate, a flexible alignment guide would be beneficial.

In various embodiments, a flexible alignment guide intended for use with flexible plates is provided. Embodiments herein employ a novel technique where a portion of the guidance device employs a flexible section, such as a section of reduced cross-sectional thickness, to increase the flexibility of the section. The flexible section of the alignment guide would be located and oriented in a manner to mirror the flexible section of the corresponding bone plate. To impart flexibility, other embodiments may use sections of low modulus materials such as elastomers to join instrument sections of greater rigidity.

In various embodiments, the flexible alignment guide may be made of polymeric materials, such as Radel (polyphenylsulfone) or nylon, or metallic biocompatible materials, such as titanium or stainless steel. In various embodiments, the instrumentation may be made by injection molding of plastic/polymers, but may also be manufactured by standard machining methods or additive techniques.

Thus, an embodiment provides a flexible orthopedic guide, including a base having a first side section, a second side section, and a flexible middle section; at least one coupler for coupling the flexible orthopedic instrument to a bone plate; and a plurality of alignment cavities aligned with corresponding holes in the bone plate, wherein the flexible orthopedic instrument stays temporarily engaged with the bone plate through a range of flexion of both the bone plate and the flexible orthopedic instrument.

In embodiments, the middle section of the base of the orthopedic guide has a thickness of about 0.5-10 mm, while the thickness of the first and/or second side sections may also be about 0.5-10 mm. But, in an embodiment, the thickness of the middle section would be less than the thickness of the first and/or second side sections so that the middle section is a region of preferred flexing compared to the first and/or second side sections. In an example, the middle section may have a thickness of 0.5-2.0 mm and the first and/or second side sections may have a thickness of 2.5-4.0 mm.

The bone plate 100 shown in FIG. 1 is comprised of left and right plate sections 101, 102 intended to be affixed to a bone, such as a sternum on opposing sides of a sternal osteotomy. The two plate sections are joined by a central flexible (such as with an elastomer) portion 103 that is coupled to both plate sections to form a unitary device. The flexible orthopedic guide 110 engages the plate along the periphery, and has one or more cavities 111 oriented and located to align with the screw holes in the plate. The cavities 111 may capture the bone fasteners 120 within the guide and align them to the holes in the sternal repair plate. Alternatively, the cavities 111 may be used to align a drill or drill bit for formation of a bore in the underlying bone.

In embodiments, the one or more cavities may comprise integrated motion limiters configured to prevent a screw from advancing through the instrument without intervention from a user.

FIG. 2A shows a longitudinal end view of plate 200 prior to assembly with the flexible orthopedic guide 210, where the elastomer 203 is located between and bonded to the plate sections 201, 202.

The flexible orthopedic guide 210 includes a base 212 having a first side section 213, a second side section 214, and a flexible middle section 211. As shown, the middle section 211 has a reduced cross-section, thus allowing it to preferentially bend along the longitudinal axis.

FIG. 2B shows a longitudinal end view of plate 200 after assembly with the flexible orthopedic guide 210 such that the components are in contact at surface 205. The middle section 211 is positioned at the center and in-plane with the elastomer section 202 such that the flexible guide will flex in a similar manner as plate 200.

FIG. 2C shows a longitudinal end view of plate 200 after assembly of the flexible orthopedic guide 210 and plate 200, and bending of plate 200 centered at the middle section 211 and flexible plate section 202.

In FIGS. 2A-2C, orthopedic guide 210 is provided with flexibility by the presence of middle section 211 having a reduced cross-section. However, section 211 may also be a section of a flexible material, such as a low modulus material, such as an elastomer, regardless of the thickness of the material as compared to the side sections 213 and 214.

Figure 3:
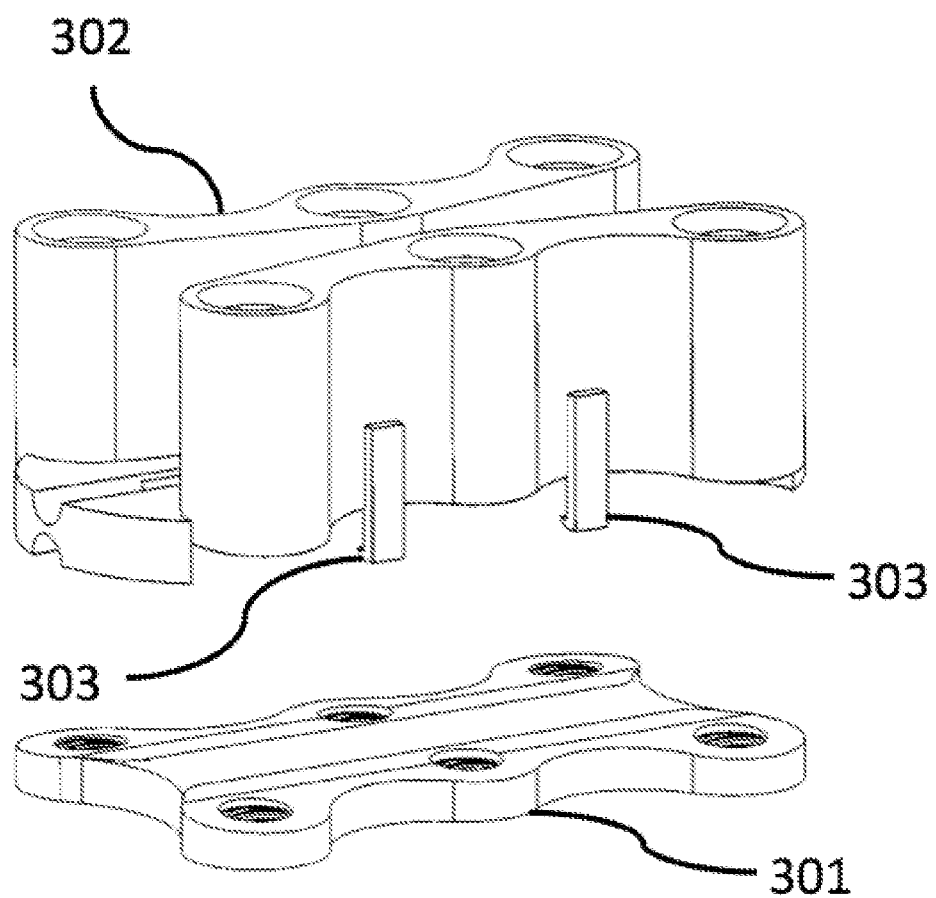
FIG. 3 illustrates a flexible clip engagement mechanism that affixes the alignment guide to the plate along the periphery of the plate.

FIG. 3 shows a perspective view of the orthopedic guide 302 with couplers, such as flexible clips, 303, which are designed to engage the plate 301 sufficiently to hold the components together during normal use. After use, the user can disengage the screw guide from the plate 301 by applying additional lateral force to bend the clips and disengage the components. The couplers 303 may also be rotated out of position when configured with a pivot, such as a spring-loaded lever. In other embodiments, the orthopedic guide 302 may be temporarily coupled to plate 301 using other mechanisms, such as snaps or rails, such as using features present on the body of plate 301 that correspond to features on orthopedic guide 302.

What is claimed is:

1. A flexible orthopedic guide, comprising:
   a base having a first side section, a second side section, and a flexible middle section, wherein the flexible middle section comprises an elastomer;
   at least one coupler for coupling the flexible orthopedic guide to a bone plate, wherein the at least one coupler is configured to engage an edge of the bone plate; and
   a plurality of alignment cavities configured to be aligned with corresponding holes in the bone plate,
   wherein the flexible orthopedic guide stays temporarily engaged with the bone plate through a range of flexion of both the bone plate and the flexible orthopedic guide.

2. The flexible orthopedic guide of claim 1, wherein the alignment cavities are coupled to the first and/or second side sections of the base.

3. The flexible orthopedic guide of claim 1, wherein the alignment cavities are extensions of the first and/or second side sections of the base.

4. The flexible orthopedic guide of claim 1, wherein the plurality of alignment cavities are aligned to permit a fastener, screw, drill, and/or drill bit to be inserted into and/or through the cavities.

5. The flexible orthopedic guide of claim 1, wherein the at least one coupler is a clip.

6. The flexible orthopedic guide of claim 1, wherein the flexible orthopedic guide comprises a metallic or polymeric material.

7. The flexible orthopedic guide of claim 1, wherein the flexible middle section comprises a thickness that is less than a thickness of the first and second side sections to permit preferential bending at the flexible middle section compared to the first and second side sections.

* * * * *